(12) United States Patent
Galopin et al.

(10) Patent No.: US 8,263,046 B2
(45) Date of Patent: Sep. 11, 2012

(54) N-PHENYL-N-PYRIDINYL-BENZAMIDES AND BENZENESULFONOMIDES HAVING COOLING PROPERTIES

(75) Inventors: Christophe C. Galopin, Chesterfield, VA (US); Lori W. Tigani, Salisbury, MD (US); Jay Patrick Slack, Loveland, OH (US); Pablo Victor Krawec, Cincinnati, OH (US); Lucienne Cole, Cincinnati, OH (US)

(73) Assignee: Givaudan S.A., Vernier (CH)

( * ) Notice: Subject to any disclaimer, the term of this patent is extended or adjusted under 35 U.S.C. 154(b) by 1149 days.

(21) Appl. No.: 12/090,801

(22) PCT Filed: Oct. 23, 2006

(86) PCT No.: PCT/CH2006/000592
§ 371 (c)(1),
(2), (4) Date: May 20, 2008

(87) PCT Pub. No.: WO2007/048265
PCT Pub. Date: May 3, 2007

(65) Prior Publication Data
US 2008/0253974 A1      Oct. 16, 2008

Related U.S. Application Data

(60) Provisional application No. 60/729,920, filed on Oct. 25, 2005.

(51) Int. Cl.
*A61K 9/68*      (2006.01)
*A61K 8/00*      (2006.01)
*A61K 31/74*    (2006.01)
*A61K 8/02*      (2006.01)
*A61K 38/00*    (2006.01)

(52) U.S. Cl. ...... 424/48; 424/49; 424/78.02; 424/78.03; 424/401; 514/18.6; 514/18.8

(58) Field of Classification Search .................. 424/49, 424/78.02, 78.03, 401, 48; 514/18.6, 18.8
See application file for complete search history.

(56) References Cited

U.S. PATENT DOCUMENTS

| | | | |
|---|---|---|---|
| 3,516,943 A | 6/1970 | Brynko et al. | |
| 4,150,052 A | 4/1979 | Watson et al. | |
| 4,285,984 A | 8/1981 | Huber | |
| 5,759,599 A | 6/1998 | Wampler et al. | |
| 6,039,901 A | 3/2000 | Soper et al. | |
| 6,045,835 A | 4/2000 | Soper et al. | |
| 6,056,949 A | 5/2000 | Menzi et al. | |
| 6,106,875 A | 8/2000 | Soper et al. | |
| 6,123,974 A | 9/2000 | Gautschi et al. | |
| 6,222,062 B1 | 4/2001 | Anderson et al. | |
| 6,306,818 B1 | 10/2001 | Anderson et al. | |
| 6,325,859 B1 | 12/2001 | De Roos et al. | |
| 6,325,951 B1 | 12/2001 | Soper et al. | |
| 6,335,047 B1 | 1/2002 | Daniher et al. | |
| 6,348,618 B1 | 2/2002 | Anderson et al. | |
| 6,387,431 B1 | 5/2002 | Gautschi | |
| 6,426,108 B1 | 7/2002 | Gautschi | |
| 6,436,461 B1 | 8/2002 | Bouwmeesters et al. | |
| 6,440,912 B2 | 8/2002 | McGee et al. | |
| 6,451,366 B1 | 9/2002 | Daniher et al. | |
| 6,482,433 B1 | 11/2002 | De Roos et al. | |
| 6,610,346 B1 | 8/2003 | Acuna et al. | |
| 6,689,740 B1 | 2/2004 | McGee et al. | |
| 6,805,893 B2 | 10/2004 | Acuna et al. | |
| 6,869,923 B1 | 3/2005 | Cunningham et al. | |
| 7,030,273 B1 | 4/2006 | Sun | |
| 2001/0008635 A1 | 7/2001 | Quellet et al. | |
| 2002/0081370 A1 | 6/2002 | Daniher et al. | |
| 2003/0082272 A1 | 5/2003 | Bouwmeesters et al. | |

(Continued)

FOREIGN PATENT DOCUMENTS
EP          1 493 336 A2      1/2005
(Continued)

OTHER PUBLICATIONS

Chem Drug.com: Oprea1__381366 (http://translate.google.com/translate?hl=en&sl=zh-CN&tl=en&u=http%3A%2F%2Fwww.chemdrug.com%2Fdatabases%2F10__3__fycbxyvrnuvnqtdk.html). 2004.*

PubChem (4-chloro-N-phenyl-N-(2-pyridin-2-ylethyl)benzenesulfonamide Hydrochloride—Compound Summary (CID 2796910)—Date: Jul. 19, 2005).*

H.R. Watson, et al., "New Compounds with the Menthol Cooling Effect," Journal of the Society of Cosmetic Chemists, New York, NY, U.S., vol. 29, No. 4, 1978, pp. 185-200.

*Primary Examiner* — Frederick Krass
*Assistant Examiner* — Chris Simmons
(74) *Attorney, Agent, or Firm* — Curatolo Sidoti Co., LPA; Joseph G. Curatolo; Salvatore A. Sidoti

(57) ABSTRACT

Used as cooling agents are the compounds of formula (I), wherein Y is carbonyl (C(=O)) or sulfonyl (SO$_2$—); and X is OCH$_3$, CN, C(=O)NHR, C(=O)OR, or halogen; and R is hydrogen or C$_1$-C$_4$ alkyl.

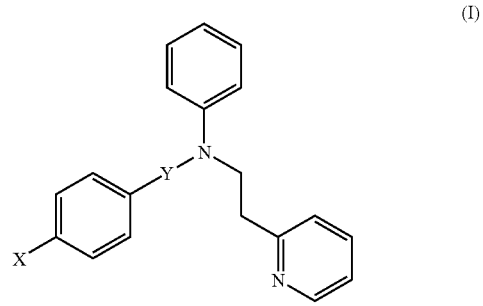

(I)

15 Claims, No Drawings

U.S. PATENT DOCUMENTS

| | | |
|---|---|---|
| 2003/0165587 A1 | 9/2003 | Binggeli et al. |
| 2004/0047960 A1 | 3/2004 | Acuna et al. |
| 2005/0004214 A1 | 1/2005 | Dewis et al. |
| 2005/0214337 A1 | 9/2005 | McGee et al. |
| 2005/0227906 A1 | 10/2005 | Schudel et al. |
| 2005/0233042 A1 | 10/2005 | Galopin et al. |
| 2006/0035008 A1 | 2/2006 | Virgallito et al. |
| 2006/0154850 A1 | 7/2006 | Quellet et al. |
| 2006/0172917 A1 | 8/2006 | Vedantam et al. |

FOREIGN PATENT DOCUMENTS

| | | |
|---|---|---|
| GB | 1 421 744 A | 1/1976 |
| WO | WO 01/03825 A | 1/2001 |
| WO | WO 2004/034791 A | 4/2004 |
| WO | WO 2005/049553 A | 6/2005 |
| WO | WO 2006/056096 A | 6/2006 |
| WO | WO 2006/092074 A | 9/2006 |
| WO | WO 2006/099762 A | 9/2006 |

* cited by examiner

N-PHENYL-N-PYRIDINYL-BENZAMIDES AND BENZENESULFONOMIDES HAVING COOLING PROPERTIES

CROSS REFERENCE TO RELATED APPLICATIONS

This application is a national stage application of International Application No. PCT/CH2006/000592, filed Oct. 23, 2006, which claims the benefit of Application No. 60/729,920, filed Oct. 25, 2005 from which applications priority is claimed, and which are incorporated herein by reference.

The present invention relates to substituted N-phenyl-N-pyridinyl-benzamides and N-phenyl-N-pyridinyl-benzenesulfonamides having cooling properties. The present invention refers furthermore to a process for their production and to consumer products comprising them.

In the flavor and fragrance industry there is an ongoing demand for compounds having unique cooling properties that provide the user with a pleasing cooling effect and which are suitable for use in a variety of products, particularly in ingestible and topical products.

Cooling compounds, that is, chemical compounds that impart a cooling sensation to the skin or the mucous membranes of the body, are well known to the art and are widely used in a variety of products such as foodstuffs, tobacco products, beverages, chewing gum, dentifrices, mouthwashes and toiletries.

One cooling compound that has enjoyed substantial success is N-ethyl p-menthanecarboxamide (WS-3) and is thus often used as benchmark. Surprisingly it has been found that certain N-phenyl-N-pyridinyl-benzamide derivatives and N-phenyl-N-pyridinyl-benzenesulfonamide derivatives exhibit cooling intensities similar to those of WS-3.

Thus the present invention refers in one of its aspects to the use as a cooling agent of a compound of formula (I)

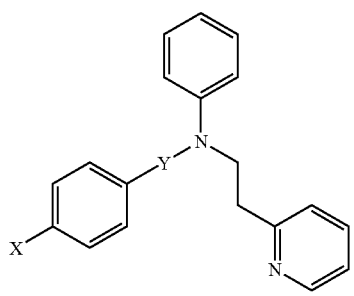

(I)

wherein
Y is carbonyl (—C(=O)—) or sulfonyl (—SO$_2$—);
X is —O—CH$_3$, —CN, —C(=O)NHR, —C(=O)OR, a halogen, e.g. chlorine;
R is hydrogen or C$_1$-C$_4$ alkyl, e.g. ethyl, or isopropyl.

In particular embodiments are compounds of formula (I) selected from the list consisting of 4-methoxy-N-phenyl-N-[2-(pyridin-2-yl)ethyl]benzamide, 4-methoxy-N-phenyl-N-[2-(pyridin-2-yl)ethyl]benzenesulfonamide, 4-chloro-N-phenyl-N-[2-(pyridin-2-yl)ethyl]benzenesulfonamide and 4-cyano-N-phenyl-N-[2-(pyridin-2-yl)ethyl]benzenesulfonamide.

The compounds of formula (I) may be used in products that are applied to mucous membranes such as oral mucosa, or the skin, to give a cooling sensation. By "applying" is meant any form of bringing into contact, for example, oral ingestion or, in the case of tobacco products, inhalation. In the case of application to the skin, it may be, for example, by including the compound in a cream or salve, or in a sprayable composition. There is therefore also provided a method of providing a cooling effect to the mucous membrane or skin by applying thereto a product comprising an effective amount of a compound as hereinabove described.

Products that are applied to the oral mucosa may include foodstuffs and beverages taken into the mouth and swallowed, and products taken for reasons other than their nutritional value, e.g. tablets, mouthwash, throat sprays, dentifrices and chewing gums. Products that are applied to the skin may be selected from perfumes, toiletries, lotions, oils and ointments, applicable to the skin of the human body, whether for medical or other reasons. Accordingly, in a further aspect there is provided a composition comprising an amount of at least one compound of formula (I) sufficient to stimulate the cold receptors in the areas of the skin or mucous membrane with which the composition comes into contact and thereby promote the desired cooling effect. A cooling effect may be achieved upon application of a product, for example, mouthwash or chewing gums, to the mucous membrane, e.g. oral mucosa, comprising less than 5000 ppm, in certain embodiments between 300 and 3000 ppm, such as about 1500 ppm, of a compound of formula (I). If used for beverages the addition of about 15 ppm may be sufficient to achieve a cooling effect.

Thus there is further provided an end-product selected from the group consisting of topical products, oral care products, nasal care products, toilet articles, ingestible products and chewing gum, which comprises a product base and an effective amount of at least one cooling compound of formula (I).

The compounds as hereinabove described may be used alone or in combination with other cooling compounds known in the art, e.g. menthol, menthone, isopulegol, N-ethyl p-menthanecarboxamide (WS-3), N,2,3-trimethyl-2-isopropylbutanamide (WS-23), menthyl lactate, menthone glycerine acetal (Frescolat® MGA), mono-menthyl succinate (Physcool®), mono-menthyl glutarate, O-menthyl glycerine (CoolAct® 10) and 2-sec-butylcyclohexanone (Freskomenthe®).

Whereas a CAS number has been allocated to the compound of formula (I) wherein Y is sulfonyl and X is chlorine but no reference is given, the other compounds falling within formula (I) have not been described, and are novel.

Thus, in a further aspect there is provided a compound of formula (I)

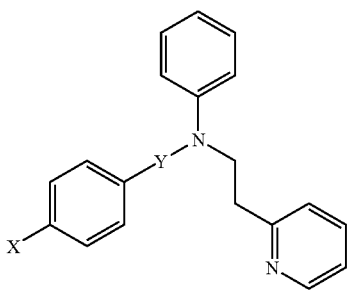

(I)

wherein
Y is carbonyl (—C(=O)—) or sulfonyl (—SO$_2$—);
X is —O—CH$_3$, —CN, —C(=O)NHR, —C(=O)OR, a halogen, e.g. chlorine;

R is hydrogen or $C_1$-$C_4$ alkyl, e.g. ethyl, or isopropyl;

with the proviso that Y is not sulfonyl if X is chlorine.

The compounds of formula (I) can be prepared by the reaction of the appropriate acyl chloride and sulfonyl chloride respectively with commercially available 2-(2-anilinoethyl)-pyridine.

The compositions and methods are now further described with reference to the following non-limiting examples.

These examples are for the purpose of illustration only and it is understood that variations and modifications can be made by one skilled in the art without departing from the spirit and the scope of the invention. It should be understood that the embodiments described are not only in the alternative, but can be combined.

EXAMPLE 1

4-Methoxy-N-phenyl-N-[2-(pyridin-2-yl)ethyl]benzamide

In a 25 ml round-bottom flask 0.085 p-anisoyl chloride and 0.04 mL of pyridine are dissolved in 3 ml of MTBE. To this solution was added 0.10 g of 2-(2-anilinoethyl)pyridine. The solution is stirred at room temperature for 24 h. To the solution was added 5 mL of water. The organic layer was separated and washed with 5 mL of water. The organic layer was dried over MgSO4. The solvent was evaporated to yield a brown oil. The oil was purified on silica gel to afford 0.15 g of an off-white solid with the following spectroscopic properties:

1H NMR (CDCl$_3$, 300 MHz) δ in ppm: 8.47 (d, 1H), 7.60 (t, 1H), 7.53 (d, 2H), 7.36-7.3 (m, 3H), 7.2-7.0 (m, 4H), 6.91 (d, 2H), 3.98 (t, 2H), 3.87 (s, 3H), 2.98 (t, 2H)

13C NMR (CDCl$_3$, 75 MHz) δ in ppm: 162.8, 158.4, 149.2, 139.4, 136.2, 128.9, 127.7, 123.5, 121.4, 113.8, 55.5, 50.2, 37.4

GC/MS (EI): 276 ($M^+$-picolinyl), 197, 171, 94, 77

EXAMPLE 2

4-Methoxy-N-phenyl-N-[2-(pyridin-2-yl)ethyl]benzenesulfonamide

To a 25 ml round bottom flask, 0.21 g 4-methoxybenzenesulfonyl chloride and 0.08 mL of pyridine were dissolved in 10 ml of MTBE. To this solution was added 0.2 g of 2-(2-anilinoethyl)pyridine. The reaction was heated at reflux for one hour and then let cool down to room temperature. To the reaction was added 10 mL of water. The organic layer was separated and washed with 10 mL of water. The organic layer was dried over MgSO4, filtered, and concentrated to yield a brown oil. The oil was purified on silica gel to recover 0.3 g of a tanned solid with the following spectroscopic properties:

1H NMR (CDCl$_3$, 300 MHz) δ in ppm: 8.47 (d, 1H), 7.60 (t, 1H), 7.53 (d, 2H), 7.36-7.3 (m, 3H), 7.2-7.0 (m, 4H), 6.91 (d, 2H), 3.98 (t, 2H), 3.87 (s, 3H), 2.98 (t, 2H)

13C NMR (CDCl$_3$, 75 MHz) δ in ppm: 162.8, 158.4, 149.2, 139.4, 136.2, 128.9, 127.7, 123.5, 121.4, 113.8, 55.5, 50.2, 37.4

GC/MS (EI): 276 ($M^+$-picolinyl), 197, 171, 94, 77

EXAMPLE 3

The following compounds have been also prepared according to the general procedure as described in Example 2.

a) 4-Chloro-N-phenyl-N-[2-(pyridin-2-yl)ethyl]benzenesulfonamide

GC/MS (EI): 280 and 282 ($M^+$-picolinyl), 197, 171, 94, 77 b) 4-Cyano-N-phenyl-N-[2-(pyridin-2-yl)ethyl]benzenesulfonamide

GC/MS (EI): 271 ($M^+$-picolinyl), 197, 94, 77

EXAMPLE 4

Experiments on Cooling Properties/Intensities

A group of panelists had been asked to taste various aqueous solutions of compounds of formula (I) and indicate which solutions had a cooling intensity similar or slightly higher than that of a solution of l-menthol at 2 ppm. The results are shown in Table 1.

TABLE 1

Experiments on cooling intensity

| Chemical | Concentration | Odor |
|---|---|---|
| Comparison: l-Menthol, 2 ppm solution | | Minty |
| N-ethyl p-menthanecarboxamide (WS-3) | 1.5 ppm | None |
| Formula (I), X = —O—CH$_3$, Y = carbonyl (compound of Example 1) | 1.5 ppm | None |
| Formula (I), X = —O—CH$_3$, Y = sulfonyl (compound of Example 2) | 2 ppm | None |
| Formula (I), X = Cl, Y = sulfonyl (compound of Example 3a) | 2 ppm | None |

EXAMPLE 6

Application in Toothpaste

| | |
|---|---|
| Opaque toothgel | 92.0 g |
| 4-Methoxy-N-phenyl-N-[2-(pyridin-2-yl)ethyl]benzamide (2% (w/w) solution in propylene glycole) | 7.5 g |
| Peppermint oil, Terpeneless | 0.5 g |

The chemicals are mixed in the toothgel, a piece of toothgel is put on a toothbrush and a panelist's teeth are brushed. The mouth is rinsed with water and the water is spit out. A longlasting cooling sensation is felt by the panelist in all areas of the mouth.

The invention claimed is:

1. A method of providing a cooling effect to the skin or mucous membranes by applying thereto an effective amount of a compound of formula (I)

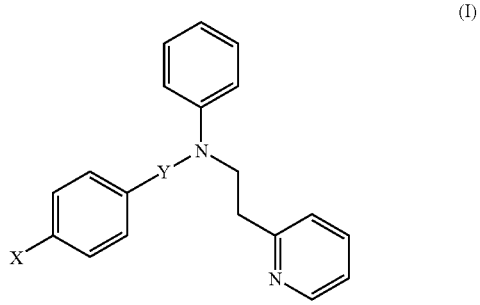

wherein

Y is carbonyl (—C(=O)—) or sulfonyl (—SO$_2$—);

X is —O—CH$_3$, —CN, —C(=O)NHR, —C(=O)OR, or halogen; and

R is hydrogen or C$_1$-C$_4$ alkyl;

with the proviso that Y is not sulfonyl if X is chlorine.

2. A method of providing a cooling effect to the skin or mucous membranes by applying thereto a product comprising at least one compound selected from the group consisting of of compounds of formula (I)

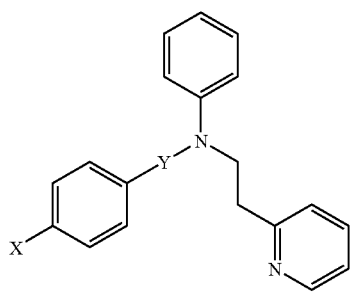

(I)

wherein

Y is carbonyl (—C(=O)—) or sulfonyl (—SO$_2$—);

X is —O—CH$_3$, —CN, —C(=O)NHR, —C(=O)OR, or halogen; and

R is hydrogen or C$_1$-C$_4$ alkyl;

with the proviso that Y is not sulfonyl if X is chlorine.

3. A product that provides a cooling effect to the skin or mucous membranes, which product comprises an effective amount of at least one compound of formula (I)

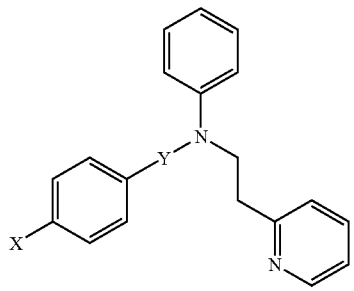

(I)

wherein

Y is carbonyl (—C(=O)—) or sulfonyl (—SO$_2$—);

X is —O—CH$_3$, —CN, —C(=O)NHR, —C(=O)OR, or halogen; and

R is hydrogen or C$_1$-C$_4$ alkyl;

with the proviso that Y is not sulfonyl if X is chlorine.

4. A product selected from the group consisting of topical products, oral care products, nasal care products, toilet articles, ingestible products and chewing gum, comprising a product base and an effective amount of a cooling compound of formula (I)

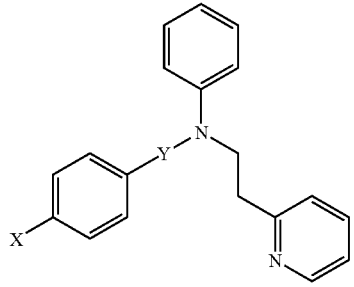

(I)

wherein

Y is carbonyl (—C(=O)—) or sulfonyl (—SO$_2$—);

X is —O—CH$_3$, —CN, —C(=O)NHR, —C(=O)OR, or halogen; and

R is hydrogen or C$_1$-C$_4$ alkyl, or a mixture thereof;

with the proviso that Y is not sulfonyl if X is chlorine.

5. A compound selected from the group consisting of 4-methoxy-N-phenyl-N-[2-(pyridin-2-yl)ethyl]benzamide, 4-methoxy-N-phenyl-N-[2-(pyridin-2-yl)ethyl]benzenesulfonamide, and 4-cyano-N-phenyl-N[2-(pyridin-2-yl)ethyl]benzenesulfonamide.

6. A method of providing a cooling effect to the skin or mucous membranes by applying thereto an effective amount of a compound which is selected from the group consisting of 4-methoxy-N-phenyl-N-[2-(pyridin-2-yl)ethyl]benzamide, 4-methoxy-N-phenyl-N[2-(pyridin-2-yl)ethyl]benzenesulfonamide, 4-chloro-N-phenyl-N-[2-(pyridin-2-yl)ethyl]benzenesulfonamide and 4-cyano-N-phenyl-N-[2-(pyridin-2-yl)ethyl]benzenesulfonamide.

7. A method of providing a cooling effect to the skin or mucous membranes by applying thereto a product comprising an effective amount of at least one compound which is selected from the group consisting of 4-methoxy-N-phenyl-N-[2-(pyridin-2-yl)ethyl]benzamide, 4-methoxy-N-phenyl-N-[2-(pyridin-2-yl)ethyl]benzenesulfonamide, 4-chloro-N-phenyl-N[2-(pyridin-2-yl)ethyl]benzenesulfonamide and 4-cyano-N-phenyl-N-[2-(pyridin-2-yl)ethyl]benzenesulfonamide.

8. The method of claim 2 wherein said applying comprises at least one of inhalation or oral ingestion.

9. A product that provides a cooling effect to the skin or mucous membranes, which product comprises an effective amount of at least one compound which is selected from the group consisting of 4-methoxy-N-phenyl-N-[2-(pyridin-2-yl)ethyl]benzamide, and 4-cyano-N-phenyl-N-[2-(pyridin-2-yl)ethyl]benzenesulfonamide.

10. A product selected from the group consisting of topical products, oral care products, nasal care products, toilet articles, ingestible products and chewing gum, comprising a product base and an effective amount of a cooling compound which is selected from the group consisting of 4-methoxy-N-phenyl-N-[2-(pyridin-2-yl)ethyl]benzamide, 4-methoxy-N-phenyl-N-[2-(pyridin-2-yl)ethyl]benzenesulfonamide, 4-chloro-N-phenyl-N-[2-(pyridin-2-yl)ethyl]benzenesulfonamide and 4-cyano-N-phenyl-N-[2-(pyridin-2-yl)ethyl]benzenesulfonamide.

11. The product of claim 4 comprising at least one of foodstuffs, beverages, tablets, mouthwash, throat sprays, dentifrices, tobacco products, perfumes, toiletries, lotions, oils, or ointments.

12. The product of claim 4 comprising at least one of a cream, a salve, or a sprayable composition.

13. The product of claim 4 further comprising an additional cooling compound.

14. The product of claim 13 wherein the additional cooling compound comprises at least one member selected from the group consisting of of menthol, menthone, isopulegol, N-ethyl p-menthanecarboxamide, N,2,3-trimethyl-2-isopropylbutanamide, menthyl lactate, menthone glycerine acetal, mono-menthyl succinate, mono-menthyl glutarate, O-menthyl glycerine or 2-sec-butylcyclohexanone.

15. The method of claim 2 wherein the product comprises a cream or salve or a sprayable composition.

* * * * *